US011310609B2

(12) United States Patent
Westermann et al.

(10) Patent No.: US 11,310,609 B2
(45) Date of Patent: *Apr. 19, 2022

(54) HEARING AID USER ACCOUNT MANAGEMENT

(71) Applicant: Widex A/S, Lynge (DK)

(72) Inventors: Soren Erik Westermann, Espergaerde (DK); Svend Vitting Andersen, Espergaerde (DK); Anders Westergaard, Herlev (DK); Niels Erik Boelskift Maretti, Birkerod (DK)

(73) Assignee: Widex A/S, Lynge (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/697,298

(22) Filed: Nov. 27, 2019

(65) Prior Publication Data

US 2020/0098475 A1 Mar. 26, 2020

Related U.S. Application Data

(63) Continuation of application No. 15/528,534, filed as application No. PCT/EP2014/075111 on Nov. 20, 2014, now Pat. No. 10,510,446.

(51) Int. Cl.
*H04R 25/00* (2006.01)
*G16H 10/60* (2018.01)
(Continued)

(52) U.S. Cl.
CPC .......... *H04R 25/554* (2013.01); *G16H 10/60* (2018.01); *G16H 10/65* (2018.01); *G16H 40/40* (2018.01);
(Continued)

(58) Field of Classification Search
None
See application file for complete search history.

(56) References Cited

U.S. PATENT DOCUMENTS

2005/0283263 A1  12/2005  Eaton
2007/0255435 A1  11/2007  Cohen
(Continued)

FOREIGN PATENT DOCUMENTS

EP  1 252 799       7/2001
EP  2 760 225 A1   7/2014
(Continued)

OTHER PUBLICATIONS

International Search Report for PCT/EP2014/075111 dated Sep. 21, 2015 [PCT/ISA/210].
(Continued)

*Primary Examiner* — Qin Zhu
(74) *Attorney, Agent, or Firm* — Sughrue Mion, PLLC

(57) ABSTRACT

A data system for handling user data for a hearing aid user and at least one hearing aid (10, 11) having a memory for storing personal settings for alleviating a hearing loss for the hearing aid user includes a remote server (25) accessible by means of an Internet enabled computer device. A personal communication device (13) is Internet enabled and is able to act as a gateway to the Internet for the at least one hearing aid. The user may create a user account on the remote server, enter personal information into the user account and store the entered personal information on the remote server, and enter the gateway information to the user account. The personal communication device and the at least one hearing aid are provided with respective transceivers for establishing a wireless connection under guidance of said application software. The least one hearing aid uploads the personal settings for alleviating the hearing loss via the gateway to the remote server for storing in the user account.

19 Claims, 5 Drawing Sheets

(51) Int. Cl.
  *G16H 10/65* (2018.01)
  *G16H 40/40* (2018.01)
  *G16H 40/67* (2018.01)
  *G16H 50/30* (2018.01)
  *H04W 4/80* (2018.01)
  *H04W 12/06* (2021.01)
  *H04W 12/069* (2021.01)
  *H04W 48/18* (2009.01)
  *H04W 76/14* (2018.01)

(52) U.S. Cl.
  CPC ............ *G16H 40/67* (2018.01); *G16H 50/30* (2018.01); *H04R 25/505* (2013.01); *H04R 25/558* (2013.01); *H04R 25/70* (2013.01); *H04W 4/80* (2018.02); *H04W 12/06* (2013.01); *H04W 12/068* (2021.01); *H04W 12/069* (2021.01); *H04W 48/18* (2013.01); *H04W 76/14* (2018.02); *H04R 2225/39* (2013.01); *H04R 2225/55* (2013.01); *H04R 2225/67* (2013.01)

(56) References Cited

U.S. PATENT DOCUMENTS

| | | |
|---|---|---|
| 2009/0047994 A1 | 2/2009 | Sommer |
| 2010/0080398 A1* | 4/2010 | Waldmann ............ H04R 25/70 381/66 |
| 2010/0330909 A1 | 12/2010 | Maddern |
| 2011/0176686 A1 | 7/2011 | Zaccaria |
| 2011/0235835 A1* | 9/2011 | Bulow .................. H04R 25/70 381/314 |
| 2011/0257994 A1 | 10/2011 | Givens et al. |
| 2012/0183164 A1 | 7/2012 | Foo et al. |
| 2012/0254987 A1 | 10/2012 | Ge |
| 2013/0243227 A1* | 9/2013 | Kinsbergen ......... H04M 1/6016 381/314 |
| 2013/0308506 A1 | 11/2013 | Kim |
| 2014/0211973 A1* | 7/2014 | Wang ................... H04R 25/505 381/315 |
| 2015/0023512 A1* | 1/2015 | Shennib ................ H04R 25/70 381/60 |
| 2015/0172831 A1 | 6/2015 | Dittberner |
| 2015/0237450 A1 | 8/2015 | Schmidt |
| 2015/0270288 A1 | 9/2015 | Yamazaki et al. |
| 2015/0296308 A1* | 10/2015 | Fluckiger ............ G06F 3/04842 715/733 |
| 2015/0351143 A1* | 12/2015 | Seymour .............. H04R 25/554 455/41.2 |
| 2016/0134742 A1* | 5/2016 | Shennib ............ H04M 1/72415 455/420 |
| 2016/0150330 A1* | 5/2016 | Niederberger ............ A61F 2/08 381/314 |
| 2016/0212552 A1* | 7/2016 | Schneider ............... H04L 67/06 |
| 2017/0180886 A1* | 6/2017 | Van Der Loo ........ H04W 12/06 |

FOREIGN PATENT DOCUMENTS

| | | |
|---|---|---|
| EP | 2 799 985 A2 | 11/2014 |
| JP | 2001-142766 A | 5/2001 |
| JP | 2014-204145 A | 10/2014 |
| WO | 2011128462 A2 | 10/2011 |
| WO | 2013/117214 A1 | 8/2013 |
| WO | 2014/094859 A1 | 6/2014 |

OTHER PUBLICATIONS

Communication dated May 22, 2018 from the Japanese Patent Office in counterpart Application No. 2017-523439.

* cited by examiner

HEARING AID USER ACCOUNT MANAGEMENT

CROSS-REFERENCE TO RELATED APPLICATIONS

The present application is a Continuation of U.S. application Ser. No. 15/528,534, filed May 22, 2017, which is a 371 of International Application No. PCT/EP2014/075111, filed Nov. 20, 2014, the disclosures of which are incorporated herein by reference.

BACKGROUND OF THE INVENTION

The present invention relates to hearing aids. The invention, more particularly, relates to a method for handling user data for a hearing aid user by creating a user account on a remote server accessible over the Internet. Also, the invention relates to a data system for handling user data.

Hearing aid manufacturing companies design, develop and manufacture hearing instruments for distribution by independent, credentialed, licensed hearing health care professionals providing service and support for hearing impaired customers in compliance with all applicable state, federal and professional regulations and law.

The hearing health care professionals are an integral part of the appropriate selection of, delivery of, and satisfaction with the hearing aid to the hearing impaired customer because they provide benefits as technical understanding of the hearing aid, individualized fitting solutions based upon the need of the individual customer and supported by professional fitting tools provided by the hearing aid manufacturing company and knowledge of hearing loss and hearing rehabilitation.

The sales channels bringing the hearing aids from the manufacturing companies to the hearing impaired customer are undergoing significant structural changes these years. We still see many specialty stores where the owner is a hearing health care professional selling and fitting hearing aids. Factory owned stores do also play a significant role, and here the hearing health care professionals play a role as employees. Supermarkets, membership warehouse clubs and discount stores have started to play a significant role in delivering hearing aids—a hearing health care professional here acts as a consultant being paid on hourly basis or receiving a fixed fee from the store. One challenge in the system is that the user buys the hearing aids, but has difficulties in changing service provider as the data belongs to the hearing health care professional or to the stores from which the hearing aid has been bought.

SUMMARY OF THE INVENTION

The purpose of the invention is to provide a data system for handling user data for a hearing aid user, by means of which the user may switch service provider when desired.

This purpose is according to the invention achieved by a method for handling user data for a hearing aid user and at least one hearing aid. The method includes creating a user account on a remote server accessible over the Internet from an Internet enabled computer device, entering personal information into the user account and storing the entered personal information on the remote server, launching application software on a personal communication device being Internet enabled, setting up a wireless connection between a hearing aid and the personal communication device under guidance of said application software, identifying in the user account the personal communication device as a gateway for the hearing aid to the Internet, and transferring data from said at least one hearing aid to the user account on the remote server via the gateway. Hereby the operator of the remote server offers hearing aid users the possibility to create a user account for managing the operation of at least one hearing aid, and to replicate vital data from the hearing aid in the account and afterwards automatically keeping the hearing aid updated.

According to a second aspect of the invention there is provided a data system for handling user data for a hearing aid user and at least one hearing aid. The data system comprises a remote server accessible over the Internet, an Internet enabled computer device for accessing the server over the Internet, a personal communication device being Internet enabled and being adapted for running application software, and at least one hearing aid. The personal communication device and the at least one hearing aid are provided with respective transceivers for establishing a wireless connection under guidance of said application software, whereby the personal communication device becomes a gateway for the hearing aid to the Internet. A client program on the Internet enabled computer device is adapted to allow the user to create a user account on the remote server, to enter personal information into the user account and store the entered personal information on the remote server, to enter gateway information to the user account. The at least one hearing aid transfers data to the user account on the remote server via the gateway.

According to a third aspect of the invention there is provided a computer-readable storage medium having computer-executable instructions, which when executed on an Internet enabled personal communication device is adapted for launching application software on the personal communication device being Internet enabled, setting up a wireless connection between at least one hearing aid and the personal communication device under guidance of said application software, whereby the personal communication device becomes a gateway for the hearing aid to the Internet, uploading gateway information to a remote server identified in said computer-executable instructions, and retrieving data from the at least one hearing aid and uploading the data to a user account on the remote server matching the gateway information.

According to a fourth aspect of the invention there is provided a personal communication device being Internet enabled and being adapted for running application software, and including a transceiver for establishing a wireless connection with at least one hearing aid under guidance of said application software, whereby the personal communication device becomes a gateway for the hearing aid to the Internet. The personal communication device uploads gateway information to a remote server identified in said computer-executable instructions, and retrieves data from the at least one hearing aid and uploading the data to a user account on the remote server matching the gateway information.

BRIEF DESCRIPTION OF THE DRAWINGS

The invention will be described in further detail with reference to preferred aspects and the accompanying drawing, in which.

DETAILED DESCRIPTION

Figure 1:
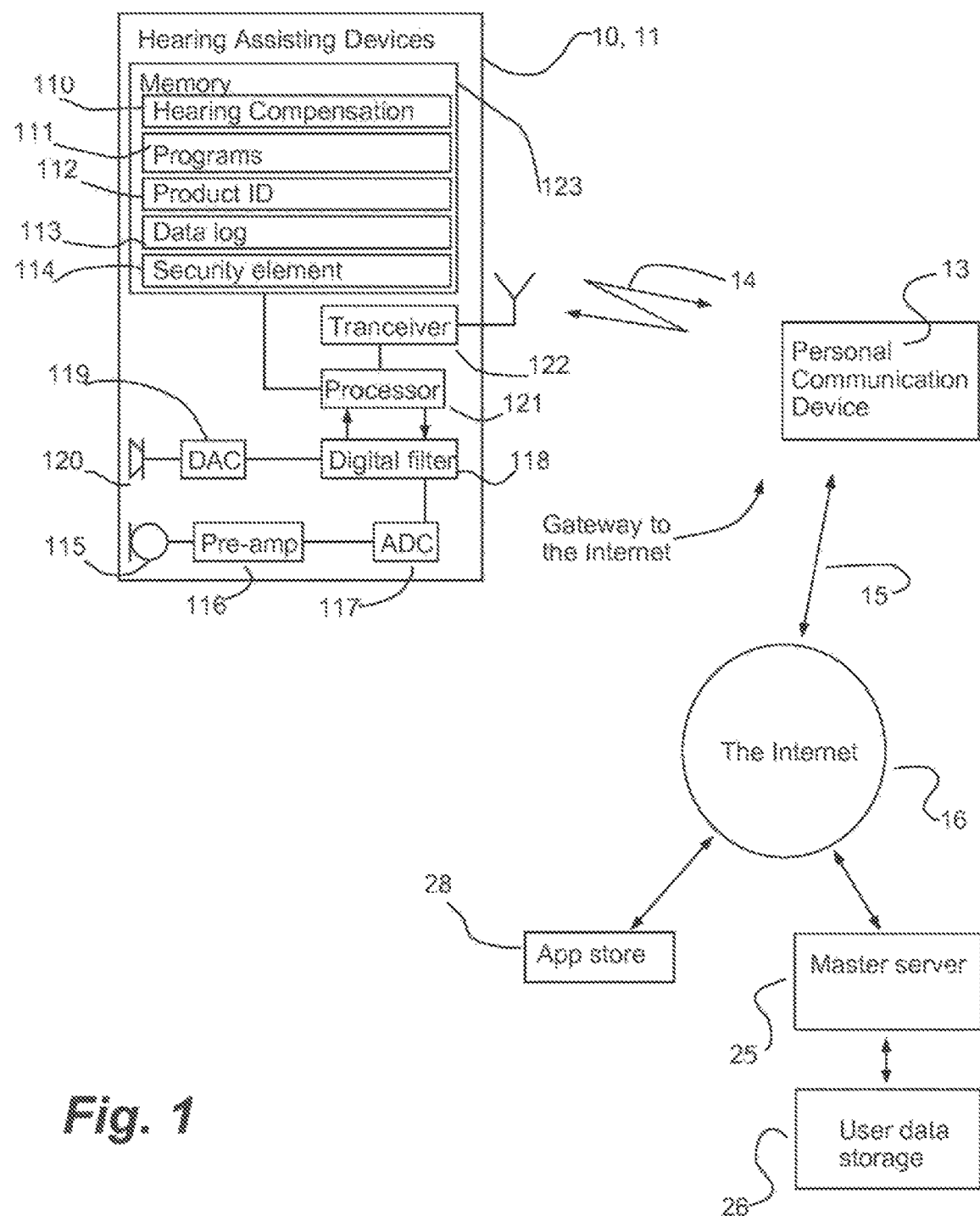
FIG. 1 illustrates schematically a data management system according to a first embodiment of the invention.

Reference is made to FIG. 1, which schematically illustrates schematically a data management system according to a first embodiment of the invention. Prior to use, the settings of the hearing aid are set and adjusted by a hearing care professional according to a prescription. The prescription is provided by an audiologist and is based on a hearing test, resulting in a so-called audiogram, of the performance of the hearing-impaired user's unaided hearing. The prescription is developed to reach a setting where the hearing aid will alleviate a hearing loss by amplifying sound at frequencies in those parts of the audible frequency range where the user suffers a hearing deficit.

Hearing aids are often provided to a hearing impaired used as a set of binaural hearing aids 10, 11. The hearing aid 10, 11 comprises an input transducer 115 or speaker for picking up the acoustic sound and converting it into electric signals. The electric signals from the input transducer 115 are amplified in a pre-amp amplifier 116 and led to an Analog-to-Digital converter (ADC) 117 for converting the analog input signal into a digital signal. The digital output signal from the Analog-to-Digital converter 117 is fed to a digital filter 118 adapted for amplifying and conditioning of the processed signal according to a predetermined setting set by an audiologist. The output from the digital filter 118 is fed to a Digital-to-Analog converter (DAC) 119 for converting the digital processed signal into an analog output signal for reproduction by an output transducer 120 or speaker. Preferably Delta-Sigma-conversion is applied in the Digital-to-Audio Conversion so the electrical output signal is formed as a one-bit digital data stream fed directly to the output transducer 120, i.e. the output converter is driven as a class D amplifier.

The digital filter 118 may advantageously include a filter bank splitting up the signal into a plurality of filter bands (often in the range of 3-15 bands or channels) being processed individually and subsequently combined into the output from the digital filter 118. A processor 121 monitors and controls the operation of the digital filter 118 according to the settings for alleviating a hearing loss by amplifying sound at frequencies in those parts of the audible frequency range where the user suffers a hearing deficit. These settings are provided by the audiologist, and the settings are stored as a data file 110 in a part of a hearing aid memory 123. In an embodiment, the hearing aid memory 123 is an EPROM or Erasable Programmable Read Only Memory, which is a non-volatile memory i.e. the type of memory chip that retains its data when its power supply is switched off. It may be achieved that only authorized personnel may edit settings for alleviating a hearing loss by applying an appropriate data access control.

The hearing aid memory 123 furthermore includes memory space 111 for storing hearing aid programs or activation codes and parameters for activating one or more hearing aid programs provided as embedded software in the hearing aid 10, 11. As these parameters relate to up and down grading of hearing aid features, it is evident that the access to editing these parameters shall be limited by applying an appropriate data access control.

The hearing aid memory 123 includes memory space 112 for storing Product ID, which may include manufacturer name, product type and serial number, and furthermore identification of the current firmware version. It is evident that an unauthorized person must not be able to change the manufacturer name, product type and serial number. This may be obtained by coding these data into the chip. Alternatively it may be achieved that only authorized personnel may edit Product ID data by applying an appropriate data access control.

Finally the hearing aid memory 123 includes memory space 113 for storing log data for the hearing aid operation and acoustical environment, and memory space 114 for storing a security element as root certificates as explained later. The hearing aid 10, 11 generates these log data automatically, and the data may be read out during a consultancy session by an audiologist when adjusting the settings for alleviating a hearing loss, or by uploading to a central server when the manufacturer of the hearing aid 10, 11 prepares for a firmware update.

The processor 121 is connected to and controls the operation of a transceiver 122. The transceiver 122 connects the hearing aid 10, 11 to a personal communication device 13 via a wireless connection 14, such as a per se known wireless communication standard like Bluetooth™ Low Energy or another appropriate protocol. The benefit of using Bluetooth™ Low Energy is that many different personal communication devices 13 like smartphones, hearing aid streamers, tablet PC's and laptops already support the standards, whereby the hearing aid 10, 11 may be paired with one of these personal communication devices 13 and use the personal communication device 13 as a gateway to the Internet. On the same time the power consumption for a transceiver 122 based upon Bluetooth™ Low Energy will be acceptable for a hearing aid design.

The personal communication device 13 according to the invention is Internet enabled which means that the personal communication device 13 may access the Internet 16 via a connection 15. The connection 15 is preferably a wired (e.g. LAN), a wireless Internet connection (e.g. WLAN such as 802.11a, b or g), or a cellular data connection (e.g. WCDMA or LTE). Advantageously, the personal communication device 13 has the ability to download and launch application software from a remote server on the internet, e. g. an app store 28. Furthermore, the personal communication device 13 will be able to access via the Internet 16 a master server 25 having user data storage 26 for maintaining and storing hearing aid user accounts.

The term "app" is short for application software which is a set of one or more programs designed to carry out operations for a specific application. Application software cannot run on itself but is dependent on system software to execute.

Figure 2:
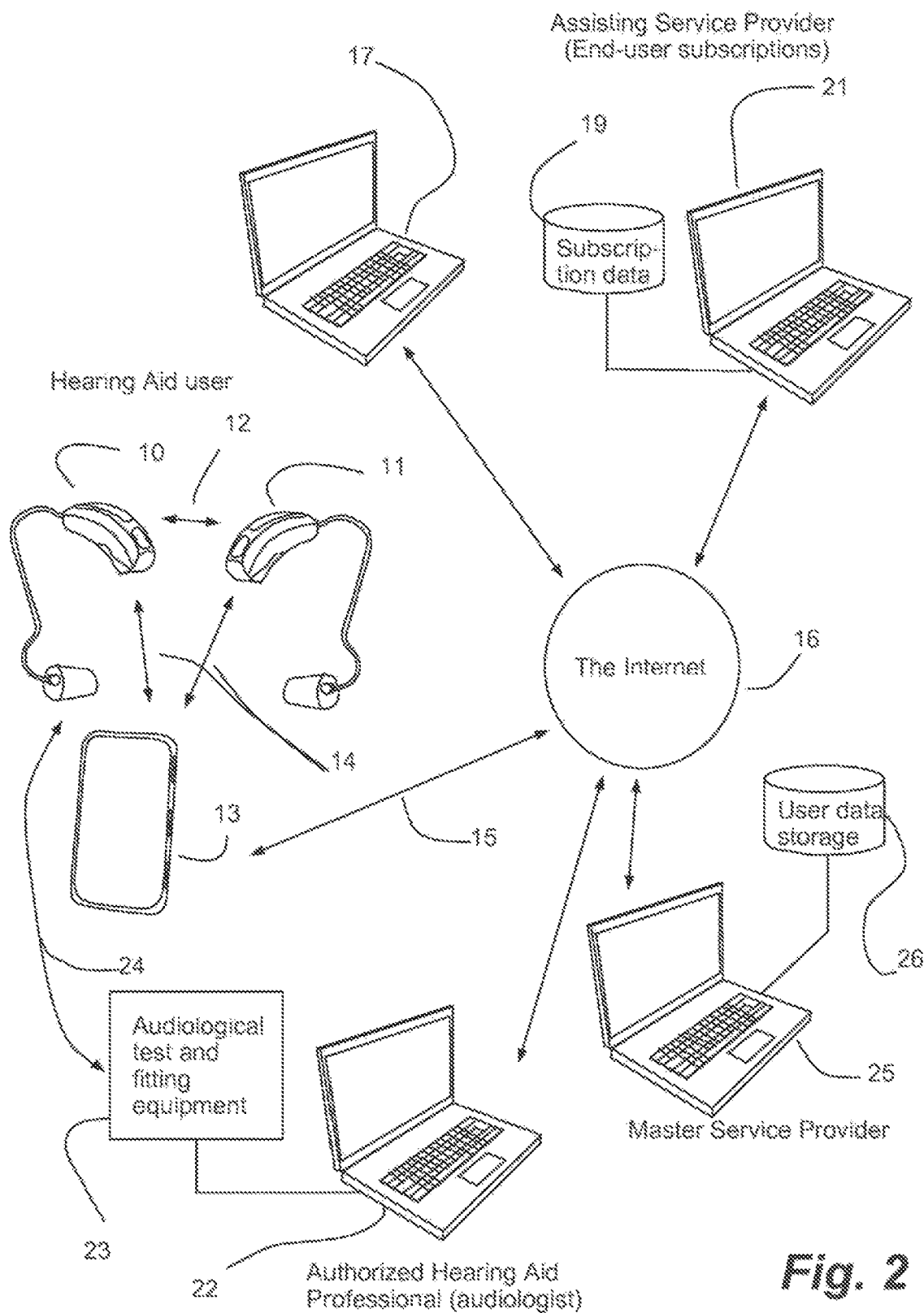
FIG. 2 illustrates schematically a data management system according to a second embodiment of the invention.

FIG. 2 shows two hearing aids 10 and 11, and these are preferably provided as a set of binaural hearing aids having and inter-ear communication channel 12 advantageously based on a proprietary communication protocol or the Bluetooth™ Low Energy protocol which is preferred for the communication between two hearing aids 10 and 11 and the personal communication device 13—here shown as a smartphone. By using a proprietary communication protocol for the inter-ear communication channel 12, it is possible to optimize the inter-ear communication channel 12 with regard to power consumption, while by using the Bluetooth™ Low Energy protocol for the inter-ear communication channel 12, it is possible to reduce the number of radios required in the hearing aid. The two hearing aids 10 and 11 are illustrated as Behind-The-Ear hearing aids having customized ear plugs. However the invention is applicable for any type of hearing aid being able to communicate with the personal communication device 13 via the wireless connection 14.

Furthermore, the hearing aid user may from a computer 17 via an appropriate Internet connection access the master server 25 having user data storage 26 for maintaining and storing hearing aid user accounts. Accessing user data stored on the master server 25 requires that the hearing aid user has the required access rights.

Entities distributing the hearing aids from the manufacturing companies to the hearing impaired customer may as assisting service providers dealing with e.g. end-user subscriptions from a computer 21 via an appropriate Internet connection access the master server 25 having user data storage 26 for maintaining and storing hearing aid user accounts—or at least relevant parts of the hearing aid user accounts. The computer 21 is connected a data storage 19 containing subscription data for a plurality of hearing impaired customers being customers at the entity. The entity may be a specialty store, a factory owned store, a supermarket, a membership warehouse club, a discount store or the like. Accessing user data stored on the master server 25 requires that the hearing aid user has the required access rights.

Finally, authorized hearing aid professionals or audiologists may from a computer 22 via an appropriate Internet connection access the master server 25 having user data storage 26 for maintaining and storing hearing aid user accounts. Accessing user data stored on the master server 25 requires that the hearing aid user has the required access rights. The authorized hearing aid professionals have audiological test and fitting equipment 23 for measuring and estimating the hearing loss of the customer, and subsequently fitting a set of hearing aids 10, 11 compensating for the unique hearing loss of the customer. As the fitting process shall fulfil the customer's needs, the process will normally take place as an interactive and iterative process. Therefor the audiological test and fitting equipment 23 is adapted for wireless communication directly with hearing aids 10, 11 via a data link 24. The data link 24 may be provided by means of a proprietary communication protocol used for the inter-ear communication channel 12, or by means of the Bluetooth™ standard, e.g. according to Bluetooth™ Low Energy protocol which is preferred for the communication between two hearing aids 10 and 11 and the personal communication device 13.

Hereby the authorized hearing aid professional will be able to write new data into and edit existing data in the data file 110 defining the hearing compensation profile in the hearing aid memory 123.

The authorized hearing aid professional will be able to edit existing data in the memory space 111 for storing status about activated hearing aid programs. The distributing entities will have read access to the content present in the data file 110 and the settings in the memory space 111 as these data are relevant for the feature set of the hearing aids and thereby for the sales price or the subscription fee the user has to pay for the using the hearing aid 10, 11 having the feature set specified by the authorized hearing aid professional. As it will be explained later, these data stored in the hearing aid 10, 11 will become uploaded to the master server where the hearing aid manufacturer can inspect the data and automatically charge the distributing entities responsible for a specific hearing aid having a feature set specified by the authorized hearing aid professional.

Figure 4:
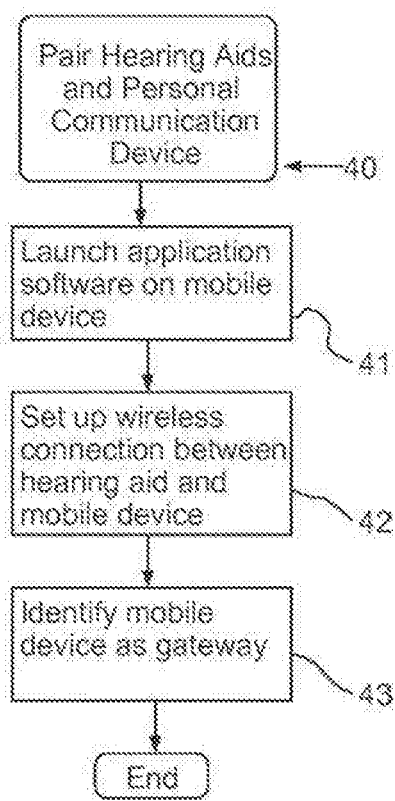
FIG. 4 illustrates a flow chart for the pairing of a hearing aid and the personal communication device according to one aspect of the invention.

According to the invention, the user pairs—in step 40 of FIG. 4—a set of hearing aids 10, 11 to a personal communication device 13, and the pairing procedure according to Bluetooth™ Low Energy protocol is well known. However, the user may advantageously choose to use special hearing aid software running on the personal communication device 13 adapted to control the pairing—as shown in step 41—and this software may either be embedded in the personal communication device 13 from the factory or be downloaded to the personal communication device 13 from the app store 28. The software app includes information about how to access (including the internet address) the master server 25. Upon pairing in step 42 of the set of hearing aids 10, 11 and the personal communication device 13, the set of hearing aids 10, 11 identifies themselves based upon information present in the product ID file 112 in the hearing aid memory. The software app running on the personal communication device 13 uploads in step 43 these data to the master server 25 based upon access information contained in the software app. Hereby the master server 25 becomes notified about that paring has taken place between the set of hearing aids 10, 11 and the personal communication device 13, and the set of hearing aids 10, 11 is identified by manufacturer, hearing aid model, serial number, software version, and the personal communication device 13 is identified (phone number and/or IP address) as gateway for accessing the set of hearing aids 10, 11.

In one embodiment, the pairing is done by bringing the personal communication device 13 via the launched application software into a searching mode, in which the personal communication device searches for hearing aids 10, 11 in pairing mode. Preferably a hearing aid 10, 11 is brought into pairing mode for a period of time by switching the hearing aid on. The hearing aid 10, 11 may preferably remain between 30 seconds and 2 minutes. The personal communication device 13 may list the hearing aids 10, 11 identified in pairing mode. Then the pairing preferably takes place by requesting the hearing aid 10, 11 to communicate a pairing code in an auditory communication, e.g. as an audio message, to the hearing aid user, and when the user has successfully entered the pairing code via a graphical user interface on the personal communication device 13, the pairing mode has been successfully completed. If the set of hearing aids 10, 11 includes a second one, the paring step is repeated for this one, too. Preferably, the hearing aids 10, 11 provide an audio indication to the user when the hearing aid enters the pairing mode, and preferably also when the pairing mode has been successfully completed.

Upon setting up a wireless connection between at least one hearing aid 10, 11 and the personal communication device 13 under guidance of application software, the master server 25 identifies in the user account the personal communication device 13 as a gateway for the hearing aid 10, 11 to the Internet 15. So far only the set of hearing aids 10, 11 and the personal communication device 13 are identified in an anonymous user account.

Figure 5:
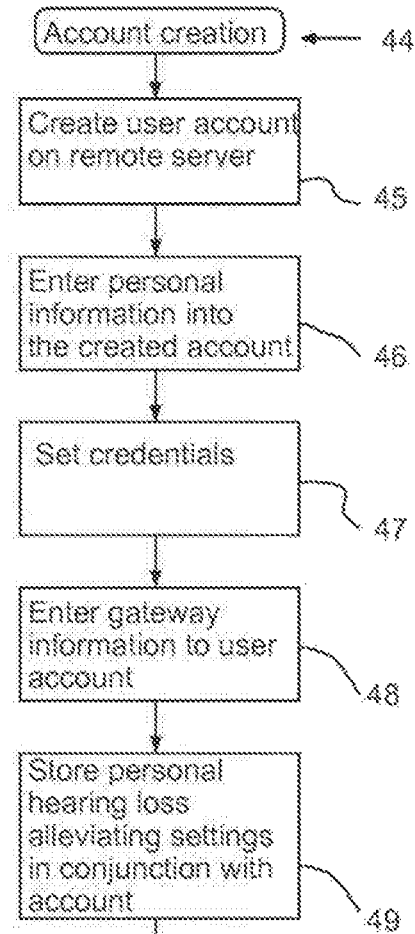
FIG. 5 illustrates a flow chart for the creation of a user account according to one aspect of the invention.

Referring to FIG. 5, it shall be explained how the user completes the account set up. Starting at step 44, the user creates a user account on the remote server 25 accessible over the Internet from the Internet enabled computer device 17, e.g. a laptop, tablet PC or a smartphone. The user enters a URL provided on the hearing aid sales package into an appropriate browser window in order to create the account at the master service provider. In the web page opened, the user may create a new account in step 45 and enter appropriate personal information in step 46. The kind of personal information included in the user account will later on be explained with reference to FIG. 3. As a part of the account set up, the user is in step 47 invited to set credentials for the account, and these credentials may in one embodiment include a username and a password—both specified by the user. Now the account has been created, the user is allowed to log off, and later on log on again for complementing the account with additional data. During the account setup, the user is invited to identify a gateway to his hearing aids 10, 11. The personal communication device 13 serves this purpose, and the user may identify the personal communication device 13 by means of e.g. its phone number or IP-address.

Once the personal communication device 13 has been identified as a gateway, the remote server 25 contacts the personal communication device 13 in order to verify its role as a gateway. This contact may preferably be done via the software app running on the personal communication device 13, and when the user has verified the gateway data, the personal communication device 13 starts to load data about the hearing aids 10, 11, such as serial number, software version and information about special hardware. Normally the hearing aids 10, 11 have been fitted in order to alleviate the hearing loss of the hearing aid user, and as a part of the account set up, the personal communication device 13 reads data from the hearing aids 10, 11, and transfers data to the remote server 25 for storing settings for alleviating the hearing loss in conjunction with the user account comprising of a data set 30 consisting of data fields 31-39.

Hereafter the remote server 25, when the hearing aids 10, 11 are online, will via the personal communication device 13 compare the settings for alleviating the hearing loss stored in the hearing aids 10, 11 and in the user data storage 26, and keep these settings synchronized. Hereby these data will be kept updated no matter whether the hearing aids 10, 11 have been updated in an off-line fitting process, or whether a new fine-tuning has been performed orchestrated by the remote server 25.

Figure 8:
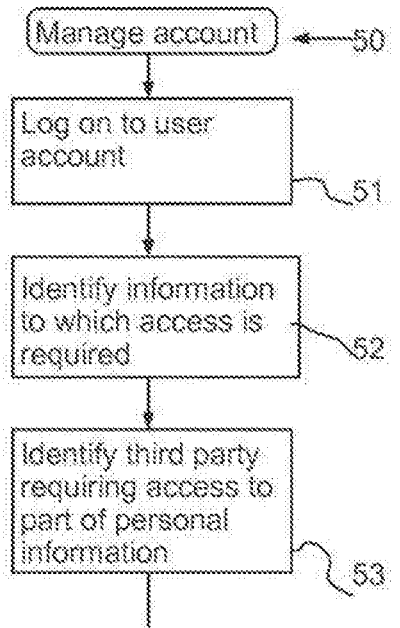
FIG. 8 illustrates a flow chart for the management of a user account according to one aspect of the invention.

The user is allowed to log off, and later on log on again for editing existing data in the account or for adding further data. With reference to FIG. 8, it will be explained how the user may manage his account in step 50. This requires that the user logs on to his account in step 51, and the web page will for this purpose have a tab named "delegate access" to the user account comprising a data set 30 consisting of data fields 31-39. In step 52, accessing certain parts of the user account will require authorization—for example when modifying the settings for alleviating the hearing loss, and the user will in step 53 only be allowed to select from a predefined list of authorized entities such as authorized audiologists or hearing aid professionals permitted to fit hearing aids. Other parts of the user account will require some commercial relationship with the hearing aid manufacturer and master service provider managing the remote server 25, and here the assisting service provider may handle the sale or a subscription or service agreement to the end-user. Also here, the assisting service provider may be selected from a predefined list of assisting service providers in step 53. The assisting service provider sells or rents a set of customized hearing aids 10, 11 to the hearing aid user, and as a part of the customization, the assisting service provider may equip the hearing with a certain number of audio processing bands and with a certain number of hearing aid programs. These features may be activated via the internet enabled computer 21 from which the assisting service provider may update his own subscription and accounting system and the user account in the remote server 25. Once the user account in the remote server 25 has been updated, the master service 25 sends the necessary activation codes to the hearing aids 10, 11 via the gateway provided by the personal communication device 13.

Preferably, the delegated access rights to the user account are only granted for a certain period of time, therefore the user sets from his Internet enabled computer device 17 the period of time in step 54 according to the needs. If the user signs up for a hearing aid subscription at a membership warehouse club, the minimum commitment period may be six or twelve months, and therefore it makes sense to automatically define the duration of the access rights to the sub-set of the dataset in a user account to be in the same range. Prior to the expiration of the access right period, the user is preferably notified about the expiration, and he may extend the access right with a similar period of time or a user defined period. The renewal of the delegated access rights takes place from the web page having the "delegate access" tab. For the fitting purpose, the audiologist may just need access to the account during the fitting session, and therefore the access rights may preferably be limited to just one day or a few days, or alternatively to just one completed session. However the user may easily extend these access rights if required by logging in to his account.

Once the user in step 55 has granted access rights to a sub-set of the personal information present in the user account via his Internet enabled computer device 17 to the third party entity, the master server 25 records the period of time for which the temporary access rights will be granted, creates in step 55 a set of credentials associated with the user account to which the temporary access rights will be granted, and notifies in step 56 the third party entity about credentials for accessing the sub-set of personal information present in the user account. The third party entity receiving the temporary access rights may be the assisting service provider operating from the internet enabled computer 21 or the authorized hearing aid professional/audiologist operating from the internet enabled computer 22.

In case the access rights relate to a fitting session with access needs for just limited time, the notification may take place as a set of e-mails with a first one linking to the user account in question and a second one containing a password for accessing the user account. A logon name may be available for the fitter in advance, included in the second e-mail or in an additional, separate e-mail.

In case the access rights are granted to an assisting service provider, e.g. a membership warehouse club, providing service to multiple hearing users via sale or subscriptions, the access rights will be granted for long term and the assisting service provider may at the same time have access to a plurality of user accounts, where assisting service providers existing login credentials provide access to the pool of sub-sets of the personal information present in the plurality of user accounts. Here the notification may take place as a notification in the browser window upon logging into the master service provider home page, and notification provides an update about new accounts that have become accessible.

Figure 3:
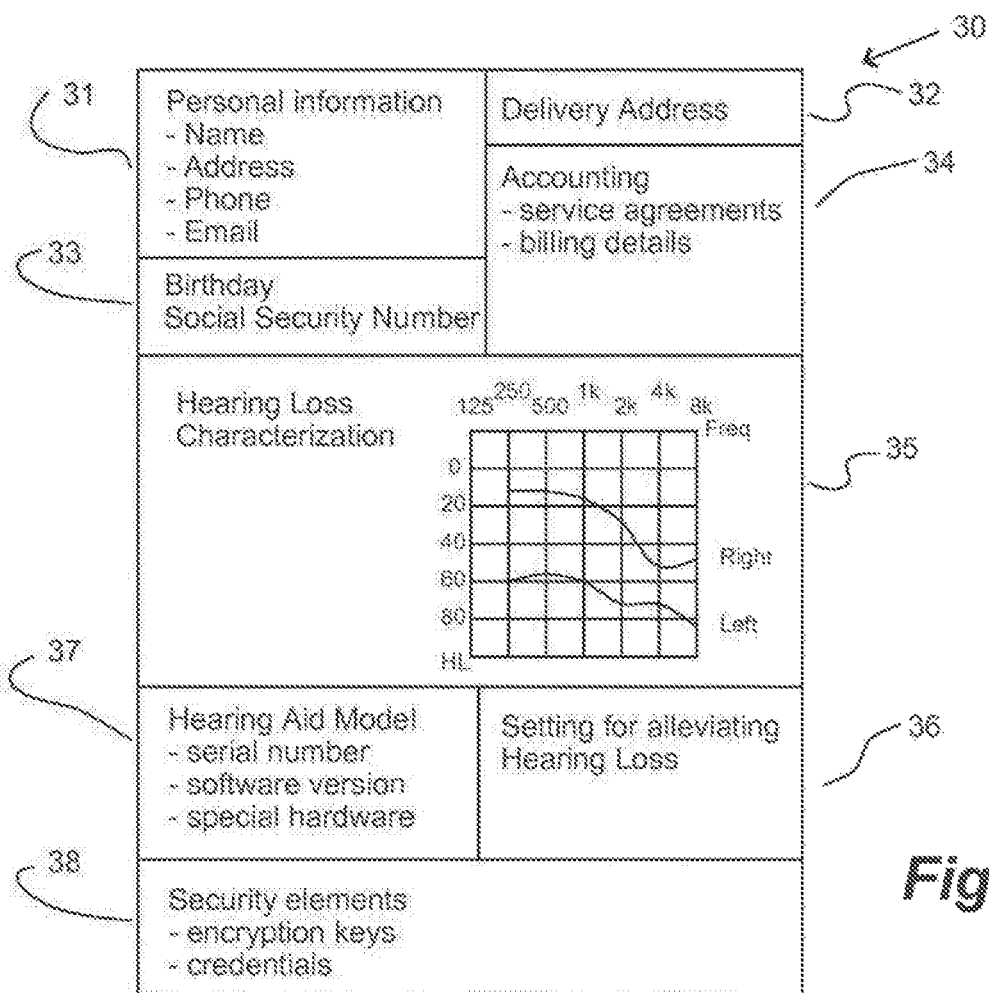
FIG. 3 illustrates schematically the data structure of a user account handled in the data management system according to an embodiment of the invention.

The master server 25 has as mentioned above user data storage 26 for maintaining and storing hearing aid user accounts, and the plurality of hearing aid user accounts defines an end-user database consisting of data developed by individual end-users. The master service provider has the Data Definition Right and is responsible for the data definition, which includes defining, modifying, and removing data structures from the database. As shown in FIG. 3, there is for each user account there defined a data set 30 consisting of data fields 31-39. The hearing aid user is as end-user permitted to update (has the Data Update Right) the data set 30, which means that he can insert, modify, and delete data. The hearing aid user is furthermore permitted to delegate the Data Update Right for his specific user account to third parties like authorized hearing aid professionals and assisting service providers, and to specify that the delegated Data Update Right relates to one or more data fields 31-39 of the data set 30, and that the delegated Data Update Right is for a specified period of time.

For each hearing aid user account there will exist some Data Retrieval Rights, which are the rights to obtain information either for end-user queries and reports or for adjusting the setting of the hearing aids. The will be some overlapping between the Data Update Right and the Data Retrieval Rights. Finally, the master service provider will according to one embodiment hold the Administration Rights for the database. The Administration Rights allows the master service provider to register and monitor user activities. The master service provider enforces data security—including grant of credentials. The master service provider maintains the lists of authorized hearing aid professionals and assisting service providers, by ensuring that the parties appearing there have been authorized. The master service provider monitors the performance of the database—including concurrency control, maintains data integrity, and recovers information if the system fails.

The data set 30 in a user account includes a personal information data field 31, which typically is the first data field filled out by the user when creating an account. The personal information includes name, address and additional contact data like phone number and e-mail address. A delivery address data field 32 defines the delivery address for hardware to be delivered to the hearing aid user. This hardware may include hearing aids returned from service, replacement hearing aids, batteries, wax guards, hearing aid drying boxes and other items ordered from the master service provider or the assisting service provider. The delivery address is specified by the owner of the account and may be identical to the home address identified in the personal information data field 31 or may identify a preferred supermarket in case the account is linked to a membership in a warehouse club. The owner of the account will have Data Update Rights to the personal information data field 31 and the delivery address data field 32, while the authorized hearing aid professionals and assisting service providers will have the Data Retrieval Rights to these data fields of the data set 30.

In a social security data field 33, the user may enter his birthday information and social security number, which may be used by the social authorities in cases these are committed to pay a part of the sales prize or subscription fees. In an accounting data field 34, the master service provider, the assisting service provider, and the authorized hearing aid professional may enter respective service agreements and the user may enter billing details, such as that an invoice is preferred or that an amount to be drawn from a specified credit card is preferred. The service agreements may refer to a specified fitting session, a hearing test, purchase of a specified set of hearing aids, subscription to a specified set of hearing aids, upgrade of an existing set of hearing aids batteries, or replacement parts. The user has the right to approve the service agreements and enter billing details, while the service providers may enter service agreement details as price and conditions supported by one or more documents and use entered billing details for their own accounting. The accounting data field 34 will only contain one service agreement, and if several service agreements are initiated, supplementing accounting data fields 34 will be created. Only parties to a service agreement do have Data Retrieval Rights.

For some of the service agreements, the database keeps the historical data so the hearing aid user may buy e.g. batteries from his smart phone by a few clicks on an app, as an existing accounting data field 34 specifies a service level agreement for batteries, the amount of batteries, the delivery address and the payment details.

When the authorized hearing aid professional or audiologist tests the hearing of a client, he obtains the results in an audiogram which is a graph showing the hearing loss measured in decibels for standardized frequencies in Hertz. The threshold of hearing is plotted relative to a standardized curve that represents "normal" hearing, in dB (HL). According to the invention the authorized hearing aid professional may store the hearing loss characterization in a dedicated Hearing Loss Characterization data field 35, whereby the authorized hearing aid professional or another authorized hearing aid professional on a later point of time may assess changes in the hearing capability of the client.

When the authorized hearing aid professional has determined the hearing loss of his client and an appropriate hearing aid has been chosen, the authorized hearing aid professional sets the hearing aid parameter in an interactive dialogue with the client by using the audiological test and fitting equipment 23 communicating directly with hearing aids 10, 11 via the wireless data link 24. When the fitting has been completed, the settings are stored in the data file 110 defining the hearing compensation profile in the hearing aid memory 123 in each of the hearing aids 10, 11. Once the settings have been updated in the hearing aid 10, 11, and the hearing aid 10, 11 identifies a gateway to the Internet 15 via the personal communication device 13, it seeks to establish a secure connection to the master server 25 for transferring these data to the data field 36 for the settings of the hearing compensation profile for each of the hearing aids 10, 11. The hearing aids are programmed to automatically place a copy of settings of the hearing compensation profile for each of the hearing aids 10, 11 in an associated user account when the settings have been updated off-line (not using the personal communication device 13 as gateway) by means of fitting equipment 23.

Preferably, the data field 36, in which the hearing compensation profiles are stored, includes historical data for the hearing compensation profile settings. Hereby the user may request a previous setting if he for some reasons find the current setting problematic in a specific sound environment or situation. The request of re-importing a previous setting may be initiated from an app on the personal communication device 13 acting as gateway.

Also the master server 25 will be able to set up a secure connection to the hearing aids 10, 11 for loading settings of the hearing compensation profile into one or more of the hearing aids 10, 11. The trigger for doing such a push of settings may as mentioned be that the user has requested a previously used setting, or that the user has received one or more replacement hearing aids directly from factory, and that these new hearing aids once these are connected to the gateway shall be equipped with appropriate programs and equipped with the appropriate hearing compensation profile settings. This will make a replacement operation easier for the client as the new hearing aids 10, 11 can be delivered by a postal or shipping company and the preparation and personalization of the hearing aids 10, 11 takes place online using a personal communication device 13 as gateway.

The authorized hearing aid professional has via his login Data Update Rights to the Hearing Loos Characterization data field 35 and the hearing compensation profile data field 36, while the owner of the account has Data Retrieval Rights to the Hearing Loss Characterization data field 35.

Preferably, the hearing aids 10, 11 are programmed to automatically upload identification details for the hearing aid to the master server 25 when the hearing aids 10, 11 are linked to a user account by means of the gateway formed by the personal communication device 13. These product ID data are read from the product ID file 112 in the hearing aid memory 123 and uploaded via the gateway and the Internet to the master server 25 and in data field 37 of the user account.

Only the hearing aids 10, 11 do have Data Update Rights to the product ID data field 37 while all having access rights to the account do have Data Retrieval Rights to the product ID data field 37.

For each user account there is provided a data field 38 containing security elements as credentials for access to one or more data fields in the hearing aid user account and secure keys for establishing a secure connection between the master server 25 and the hearing aids 10, 11. The users having access to one or more data fields of the hearing aid user account may access and edit their own user name and passwords only in the data field 38—Data Update Rights and Data Retrieval Rights—but not expand scope and duration of the temporary access rights. The master service provider holds the Administration Rights for the database and will be responsible for that the secure keys in the data field 38 together with the root certificate stored as the security element in the memory space 114 of the hearing aid memory 110 may establish a secure connection between the master server 25 and the hearing aids 10, 11.

Figure 7:
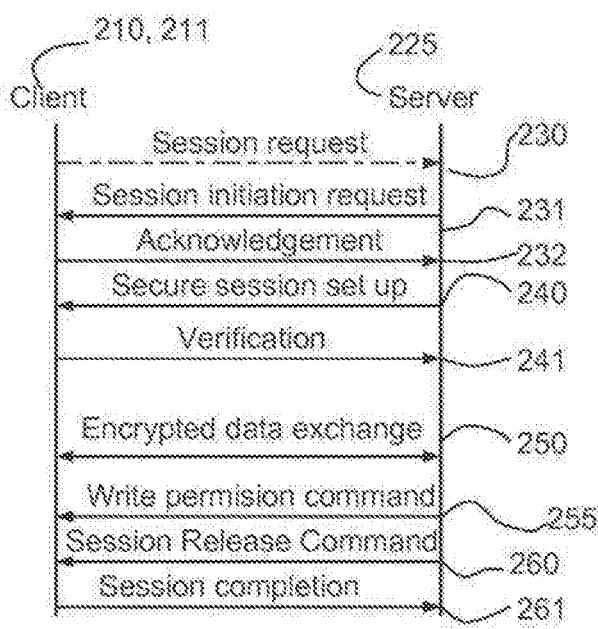
FIG. 7 illustrates the message structure for a secure session according to the invention.

The hearing aids 10, 11 are adapted to ensure that data only may be written in the hearing compensation memory space 110 and program memory space 111 when permitted by the master server 25. This takes place in a secure session as shown in FIG. 7 where encrypted data are exchanged, and where the data transfer is completed when the master server transmits a write permission command 260. Hereafter, the hearing aids 10, 11 may store appropriate data in the hearing compensation memory space 110 and program memory space 111.

Figure 6:
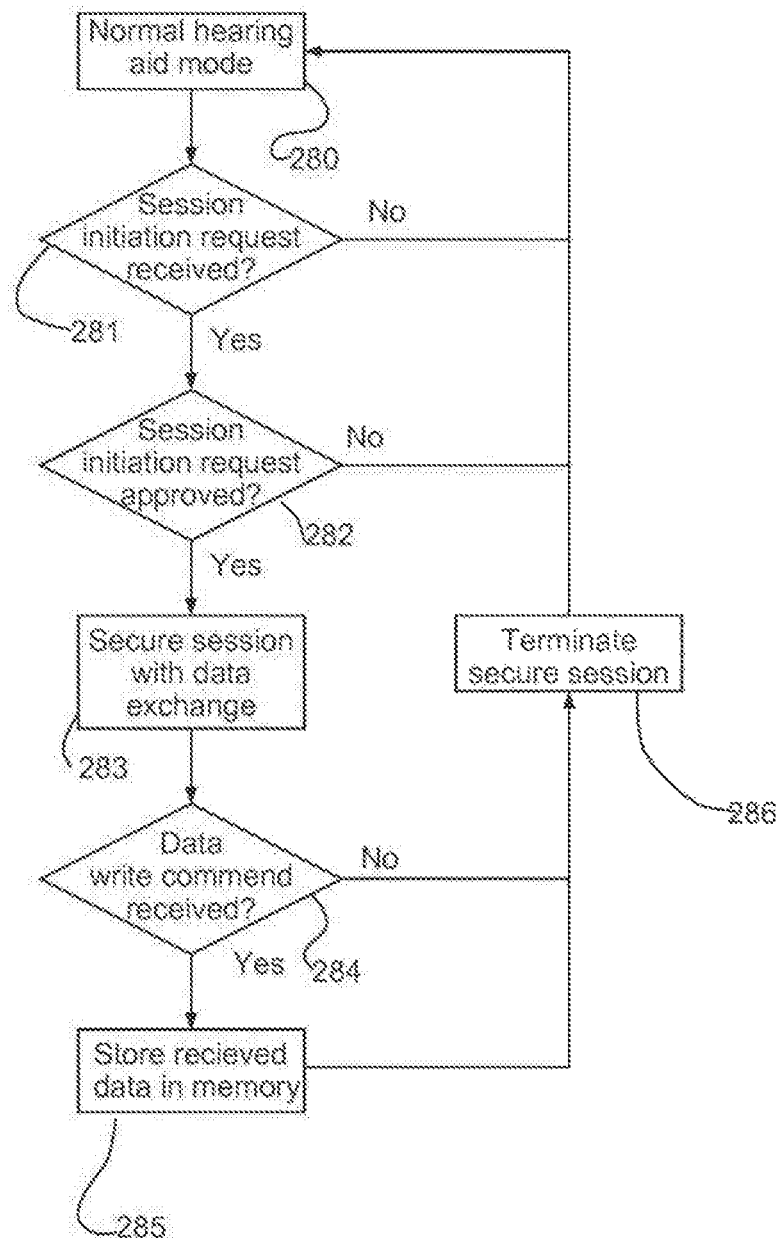
FIG. 6 illustrates a flowchart for the hearing aid during a data exchange session with a remote server according to an embodiment of the invention.

FIG. 6 shows a flowchart for the hearing aid during a data exchange session with a remote server according to the invention. In step 280, the hearing aid 10, 11 is in normal mode which means that the hearing aids reproduce amplified audio picked up from the surroundings or stream audio from an external audio source.

The message structure for a secure session according to the invention is shown in FIG. 7. The hearing aids 10, 11 are here identified as the client 210, 211, and the master server 25 as the server 225. As marked with broken line the client 210, 211 is allowed to ping (informal request) 230 the server 225 and ask it to set up a secure connection.

However, the method is based on that the server 225 sends a "Session Initiation Request" 231 to the client 210, 211. In step 281, the hearing aid 10, 11 evaluates whether such a "Session Initiation Request" has been received. If this is not the case the hearing aid 10, 11 will reassume the normal hearing aid mode in step 280. If a "Session Initiation Request" is deemed to have been received, the hearing aid user is notified on the personal communication device 13 and is allowed to postpone the data exchange, and the hearing aid 10, 11 will reassume the normal hearing aid mode in step 280. Also the battery status for the hearing aid 10, 11 is checked, and if neither the hearing aid 10, 11 nor the hearing aid user disapproves the "Session Initiation Request" in step 282, the client 210, 211 sends an "Acknowledgement" message 232 to the server 225.

The purpose of setting up a secure session is to ensure that the hearing aids 10, 11 are protected against unauthorized modifications and fraud. There exist many authentication methods that may be applied when setting up a secure session preferably employing encryption. Such authentication methods include a handshake procedure and subsequent exchange of cryptographic parameters. In one embodiment the server 225 authenticates the client 210, 211 by means of validating its IP-address which is defined by the IP address of the gateway (personal communication device 13). The server 225 initiates the secure session, and the session is set up based upon the root certificate store as the memory part 114 in the hearing aids 10, 11.

Initially, the client 210, 211 and the server 225 have to agree on a protocol version, select cryptographic algorithms, and optionally authenticate each other—which is done by the "Secure Session Set Up" message 240 and the "Verification" message 241. By using private-key encryption techniques, the client 210, 211 and the server 225 generate a shared secret that can be exchanged secretly over the Internet.

In step 283, the client 210, 211 and the server 225 exchange encrypted data 250—"Encrypted Data Exchange" marked by the arrows in both ends indicating that the traffic may go both ways. If the hearing aid 10, 11 has received data for storing, it waits for a "Write Permission" message 255 from the server 225. The "Write Permission" message 255 allows the hearing aid 10, 11 to store data in a specified part of the memory 123. In step 285, the hearing aid 10, 11 writes the received data into appropriate parts of the hearing compensation memory space 110 and program memory space 111. Hereafter the hearing aid 10, 11 will terminate the secure session in step 286 and reassume the normal hearing aid mode in step 280.

If a "Write Permission" message 255 is deemed not to have been received in step 284, the hearing aid 10, 11 will shortly after terminate the secure session in step 286 and reassume the normal hearing aid mode in step 280 without storing the received data.

The secure session is released by the server 225 sending a "Session Release Command" message 260, and the client confirms the release by sending a "Session Completion" message 261 in step 286.

According to one embodiment, the hearing aid manufacturer intends to ensure that he is the only one to communicate with the hearing aid for installing software updates and provide settings for alleviating the hearing loss for the hearing aid user. The hearing aid manufacturer will also ensure that he is the only one who can activate and deactivate features and programs in the hearing aids 10, 11 as this affects the price of the hearing aid 10, 11. Therefor the security element 114 is a digital certificate stored in the hearing aid 10, 11 during the manufacturing.

Digital certificates are verified using a chain of trust. The trust anchor for the Digital Certificate is the Root Certificate Authority. A trust anchor is an authoritative entity represented by a public key and associated data. The public key is used to verify digital signatures, and the associated data is used to constrain the types of information or actions for which the trust anchor is authoritative.

The most common type of digital certificates is based on the ITU-T X.509 standard including a digital signature from a certificate authority. The Root Certificate Authority is, according to this embodiment, the hearing aid manufacturer. Hereby the hearing aid manufacturer will be able to issue an ad hoc update for Digital Certificates for a specific set of hearing aids 10, 11, granting certain rights to adjust the settings in the hearing aids 10, 11 during a fitting session.

A Digital Certificate identifies the trust level of an entity seeking to change software or setting in a device. The master server 25 will be associated with a so-called "Trusted" root certificate allowing the master server 25 to establish a chain of trust that is used to verify other Digital Certificates signed by the trusted roots, for example to establish a secure connection to the hearing aids 10, 11. Typically these certificates will be of temporary character, and may be valid for a short period of time—days or weeks—and granted to a specified audiologist or fitter.

The Digital Certificate includes a certificate ID as certificate version, serial number and identification of the signature algorithm used, for example "SHA1 with RSA encryption" and issuer of the certificate. The trust level is indicated as well as a validity period, which includes a start and an end date. A public key for the encryption is identified together with a Certificate Signature Algorithm and a Certificate Signature.

The master server 25 may write data in 110 (adjust hearing compensation settings), 111 (activate programs and features) and 114 (update root certificates).

When the user identifies a fitter or an audiologist and updates his user account as mentioned above, the master server 25 updates the hearing aid memory 123 accordingly by loading a new Digital Certificate, or updates an existing Digital Certificate in the memory part 114 for the secure elements. The rights to enter or edit data in the hearing aid 10, 11 is by means of the new or updated root certificate temporarily delegated to the fitter or the audiologist. The fitter or audiologist is notified about the delegation of rights, when the master server 25 sends a notification of the access rights to the computer 22. As a part of the fitting software, the computer 22 has security elements allowing it to set up an off-line connection to the hearing aids 10, 11, and to include a "Write Permission" message 255 allowing the hearing aid 10, 11 to execute a write command. Then the hearing aid 10, 11 writes the received data into appropriate parts of the hearing compensation memory space 110 and program memory space 111 as explained above.

In the embodiment described above the secure session is set up based upon a Root Certificate between the master server 25 and the each of the hearing aids 10, 11. This requires that the hearing aids 10, 11 are able to handle the data encryptions themselves.

In an alternative embodiment, the personal communication device 13—e.g. a smartphone—acting as a gateway, has some inherent security tools available, which may assist the master server 25 and the hearing aid 10, 11. Preferably, the secure session is set up by means of a Mobile Virtual Private Network (VPN) whereby the authentication occurs during the establishing of a communication tunnel (tunnel establishment), and before routing data through the VPN gateway provided by the personal communication device 13.

During the secure session (tunnel mode), data is exchanged between the master server 25 and the hearing aid 10, 11 by arranging the data into an IP packet being encrypted and/or authenticated. The encrypted and/or authenticated IP packet is then encapsulated into a new IP packet with a new IP header, and transmitted between the master server 25 and the VPN gateway provided by the personal communication device 13. The communication between the personal communication device 13 and the hearing aid 10, 11 will be less critical as the personal communication device 13 and the hearing aid 10, 11 will be adjacent to each other. Furthermore, inadvertent access to the personal communication device 13 may be prohibited by an appropriate use of passwords or biometric access control.

Tunnel mode is used to create virtual private networks for remote user access (host-to-network communications). The VPN tunnel communication deals with the data security over the Internet. The security elements 114 in the hearing aid 10, 11 ensure furthermore that data received is stored only when a write command is received authenticating the origin of the data as being from the master server 25 or an entity (the computer 22) having temporary writing rights.

Other protocols providing a similar security include IPsec (Internet Protocol Security (IPsec) which is a protocol suite for securing Internet Protocol (IP) communications by authenticating and encrypting each IP packet of a communication session and SSL (Secure Sockets Layer) which is a protocol for encrypting information over the Internet.

In order to prevent fraud by means of unauthorized fitting equipment 23, the fitting session may according to the invention be based upon a delegation of the right to communicate with a hearing aid 10, 11 according to the invention. When the owner of the user account identifies an authorized hearing aid professional or audiologist to fit a set of hearing aids, the master server sends a notification of the access rights to the computer 22, and in addition to this, the master server 25 sends security elements to the computer 22. These security elements allow the computer to set up an off-line connection to the hearing aids 10, 11, and to include a "Write Permission" message 255 allowing the hearing aid 10, 11 to execute a write command. Then the hearing aid 10, 11 writes the received data into appropriate parts of the hearing compensation memory space 110 and program memory space 111 as explained above.

When a hearing aid user with a severe hearing loss at higher frequencies gets a new hearing aid, he will often be offered a transposer or compression feature. The loss of audibility of high frequency sounds often compromises speech understanding and the appreciation of music and nature's sounds. The assignee offers a program, named Audibility Extender™, moving inaudible sounds, such as high-frequency speech sounds, and environmental sounds like birdsong, a doorbell, music, etc. to a frequency region where they are audible. Based on the measured hearing loss, the audiologist is able to set the correct setting for the program but such a change will often be overwhelming for the hearing aid user, and therefore an adaptation period is required. The audiologist decides in an acclimatization strategy how the final setting for e.g. the Audibility Extender shall be reached by stepwise adjustments over several weeks. These steps may be programmed by the audiologist to take place automatically. Often a consultation at the audiologist will be required. The audiologist may still define the steps of the acclimatization strategy, but according to the invention, the changing from one step to the next (or the previous) is controlled by the hearing aid user—either from by accessing the user account from the Internet enabled computer device 17 or from the personal communication device 13.

Hearing aid users do often suffer of tinnitus, and various tools have been developed to help users relax and manage their tinnitus, e.g. Widex Zen™. The user account according to the invention may also be used for introducing new features available for the hearing aids. The hearing aid user may via the user account be offered a free trial period (e.g. one month) where the Zen™ program embedded in the hearing aid 10, 11 is activated. When the free trial period has expired, the program will become automatically disabled. However the user may enable the program again by paying an activation fee or a periodical subscription fee via his account.

The Internet enabled computer device according to the invention shall be able to access the master server 25 via an appropriate Internet connection. The computer 17 fulfilling this purpose may be a laptop or a tablet computer connected via WLAN to the Internet. In a specific embodiment, the user may access the remote server by means of his smartphone for creating the user account, and as the smart phone also serves as gateway, the very same smartphone may operate as personal communication device 13 during pairing of the short range communication, and as computer 17 during user account establishment and management.

The invention claimed is:

1. A method for programming a hearing aid, the method comprising the steps of:
creating a user account for a hearing aid user on a remote server accessible over the Internet, said hearing aid user having a hearing aid programmed with personal settings to alleviate a hearing loss of said hearing aid user;
the hearing aid user causing said personal settings to be transferred from said hearing aid into a memory associated with the user account of the hearing aid user;
identifying a hearing aid in the user account by means of a unique product ID code;
subsequently connecting the hearing aid to the Internet;
requesting the personal settings to be loaded from the user account on the remote server into the hearing aid;
transferring the personal settings from the user account on the remote server via the internet into the hearing aid, in a programming session during which both the remote server and the hearing aid are connected to the internet in overlapping time periods;
verifying whether the hearing aid has permission to store the received personal settings in the programming session; and
storing and applying the personal settings if the permission permits the programming session.

2. The method according to claim 1, wherein prior to causing said personal settings to be transferred, said personal settings are set in an interactive dialogue between an authorized hearing aid professional and the hearing aid user.

3. The method according to claim 1, wherein the identification of the hearing aid in the user account comprises identifying the hearing aid user from an internet gateway, and automatically uploading the unique product ID code from the hearing aid via the internet gateway to the user account when the hearing aid is connecting to the Internet via the internet gateway.

4. The method according to claim 1, wherein the requesting of the personal settings for alleviating a hearing loss of the hearing aid user comprises the hearing aid user requesting reload of historical personal settings as earlier transferred from the hearing aid to said memory.

5. The method according to claim 1, wherein the requesting of the personal settings for alleviating a hearing loss of the hearing aid user comprises an authorized hearing aid professional requesting updated personal settings to be loaded from the remote server into the hearing aid.

6. The method according to claim 1, wherein the verifying whether the hearing aid has permission to store the received personal settings to a memory of the hearing aid comprises verifying a trust level of the requested data exchange in a digital certificate stored in the hearing aid.

7. The method according to claim 6, wherein the storing and applying the personal settings for alleviating a hearing loss includes overwriting of the current personal settings stored in a memory of the hearing aid.

8. A system for programming a hearing aid, and comprising at least one hearing aid adapted for connecting to the Internet and a remote server accessible over the Internet,
the remote server is adapted for hosting a database including a plurality of user accounts for hearing aid users, a specific user account comprises personal settings for alleviating a hearing loss of the specific hearing aid user, and a hearing aid of the specific hearing aid user is identified in the user account by means of a unique product ID code;
wherein the remote server is adapted to
receive personal settings for alleviating a hearing loss of a specific hearing aid user via the internet from the hearing aid of the specific hearing aid user and storing said settings in the user's specific user account, and
transfer personal settings for alleviating a hearing loss of said specific hearing aid user via the internet from said specific user account to the hearing aid of the specific hearing aid user upon request, in a programming session during which both the remote server and the hearing aid are connected to the internet in overlapping time periods; and
wherein the hearing aid of the specific hearing aid user is adapted for verifying whether the hearing aid has permission to store the received personal settings received in the programming session, and for storing and applying the personal settings if the permission permits the programming session.

9. The system according to claim 8, wherein the personal settings received from the hearing aid of said specific hearing aid user are settings originating from an interactive dialogue between an authorized hearing aid professional and the hearing aid user.

10. The system according to claim 8, wherein the database having a plurality of user accounts in the remote server is adapted for receiving the unique product ID code automatically uploaded from the hearing aid via the internet gateway to the user account when the hearing aid is connecting to the Internet via the internet gateway.

11. The system according to claim 8, wherein the request is from the hearing aid user requesting a reload of historical personal settings as earlier transferred from the hearing aid to said server.

12. The system according to claim 8, wherein the request is from an authorized hearing aid professional requesting updated personal settings, different from the settings earlier transferred from the hearing aid to the server, to be loaded into the hearing aid.

13. The system according to claim 8, wherein the hearing aid has a memory for storing a digital certificate for verifying a trust level of a data exchange, and is adapted for verifying whether the hearing aid has permission to store the received personal settings to a memory.

14. The system according to claim 13, wherein the hearing aid is adapted for storing and applying the personal settings for alleviating a hearing loss by overwriting of the current personal settings stored in the memory of the hearing aid.

15. A hearing aid adapted to (i) transfer via the internet to a user account on a remote server specific personal settings for alleviating a hearing loss of a specific hearing aid user, and (ii) subsequently receive said personal settings from said user account on said server via the internet upon request in a programming session during which both the remote server and the hearing aid are connected to the internet in overlapping time periods; wherein the hearing aid has a memory for storing a digital certificate for verifying a trust level of a data exchange, and wherein the at least one hearing aid is adapted for verifying whether the hearing aid has permission for storing and applying the personal settings for alleviating a hearing loss of the hearing aid user if the permission permits the programming session.

16. The hearing aid according to claim 13, wherein the hearing aid is adapted for storing and applying the personal settings for alleviating a hearing loss by overwriting of the current personal settings stored in the memory of the hearing aid.

17. The method according to claim 1, wherein said connecting step comprises connecting the hearing aid to the internet through an internet gateway, and said transferring step comprises transferring the personal settings into the hearing aid while said hearing aid is connected to the internet through said gateway.

18. The system according to claim 8, wherein said remote server is configured to transfer said specific personal settings to the hearing aid while said hearing aid is connected to the internet through an internet gateway.

19. The hearing aid according to claim 15, wherein said hearing aid is configured to receive said specific personal settings from said remote server while said hearing aid is connected to the internet through an internet gateway.

\* \* \* \* \*